(12) United States Patent
Ma

(10) Patent No.: US 7,608,568 B2
(45) Date of Patent: Oct. 27, 2009

(54) TETRAAROMATIC DIAMINE COMPOUNDS AS ANTIOXIDANTS

(75) Inventor: Qinggao Ma, Naugatuck, CT (US)

(73) Assignee: Chemtura Corporation, Middlebury, CT (US)

( * ) Notice: Subject to any disclaimer, the term of this patent is extended or adjusted under 35 U.S.C. 154(b) by 271 days.

(21) Appl. No.: 11/706,116

(22) Filed: Feb. 13, 2007

(65) Prior Publication Data

US 2007/0272894 A1 Nov. 29, 2007

Related U.S. Application Data

(60) Provisional application No. 60/802,975, filed on May 24, 2006.

(51) Int. Cl.
  C10L 1/22 (2006.01)
  C10M 133/00 (2006.01)
(52) U.S. Cl. ...................... 508/546; 508/549
(58) Field of Classification Search ........... 508/485, 508/546; 252/182; 564/207, 208, 311, 313
  See application file for complete search history.

(56) References Cited

U.S. PATENT DOCUMENTS

| | | | |
|---|---|---|---|
| 3,293,181 A | 12/1966 | Stuart | |
| 3,397,145 A | 8/1968 | Cyba | |
| 3,442,804 A | 5/1969 | Le Suer et al. | |
| 3,509,214 A * | 4/1970 | Braid et al. ............. | 564/308 |
| 3,637,499 A | 1/1972 | Pollak | |
| 3,882,042 A | 5/1975 | McGuigan et al. | |
| 3,882,043 A | 5/1975 | McGuigan et al. | |
| 3,882,044 A | 5/1975 | McGuigan et al. | |
| 5,498,809 A | 3/1996 | Emert et al. | |

FOREIGN PATENT DOCUMENTS

| | | |
|---|---|---|
| DE | 1 918 285 | 10/1969 |
| DE | 2 250 328 | 4/1973 |
| DE | 2 250 351 | 4/1973 |
| DE | 2 250 397 | 4/1973 |
| DE | 2 250 427 | 4/1973 |
| GB | 1224653 * | 4/1968 |
| GB | 1 224 556 | 3/1971 |
| GB | 1 350 641 | 4/1974 |

OTHER PUBLICATIONS

Tanaseichuk et al. "Influence of Substituents on the Rate of Dissociation of Tetraarylhydrazines", *Journal of Organic Chemistry of the USSR*, vol. 8, No. 4, pp. 758-760, Apr. 1972. [English Abstract Included].
Zarubina, et al., "Possible preparation of antioxidant additives in dehydrocondensation reactions", *Sbornik Nauchnykh Trudov-Vsesoyuznyi Naucho-Issledovatel'skii Institu po Pererabotke Negti*, vol. 42, pp.45-49, 1982. [English Abstract Included].
Tanaseichuk et al. "Effect of substituents on the dissociation rate of tetraarylhydrazines", *Zhurnal Organicheskoi Khimii*, vol. 8, No. 4, pp. 758-760, 1972. [English Abstract Included].
Neugebauer, et al. "Aminyls. 4. Thermal decomposition of p-substituted tetraarylhydrazines", *Chemische Berichte*, vol. 104, pp. 886-889, 1971. [English Abstract Included].
Cauquis, et al. "Characteristics of cation radicals of some diaryl-5,10-dihydro-5,10-phenazines and the corresponding tetraarylhydrazines. Acid degradation of these compounds", *Tetrahedron Letters*, vol. 48, pp. 4649-4652, 1971. [English Abstract Included].
Neugebauer, et al. "Dissociation of tetraarylhydrazines", *Chemische Berichte*, vol. 98, pp. 844-850, 1965. [English Abstract Included].
Radina, et al., "Structure, properties, and ability to dissociate into free radicals of some hydrazine derivatives. The problem of connection between chemical structure and ability to form free radicals of nitrogen", *Doklady Akademii Nauk SSSR*, vol. 123, pp. 483-486, 1958. [English Abstract Included].

* cited by examiner

*Primary Examiner*—Glenn A Caldarola
*Assistant Examiner*—Pamela Weiss
(74) *Attorney, Agent, or Firm*—Jaimes Sher

(57) ABSTRACT

Tetraaromatic diamine compounds having the general formula:

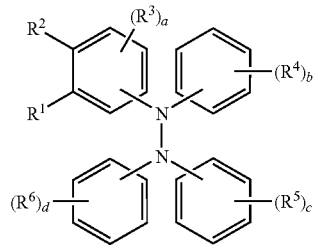

are provided wherein a is 0-3; b, c and d independently are integers from 0-5, $R^1$ and $R^2$ together with the carbon atoms to which they are bonded are joined together to form a substituted or unsubstituted $C_3$ to about $C_{30}$ ring, saturated, partially unsaturated or fully unsaturated, optionally substituted with one or more heteroatoms, a is 0-3; b, c and d independently are integers from 0-5, $R^3$, $R^4$, $R^5$ and $R^6$ are independently hydrogen, a straight or branched $C_1$-$C_{30}$ alkyl or alkylene group optionally substituted with one or more substituents, a substituted or unsubstituted $C_3$-$C_{12}$ cycloalkyl, a substituted or unsubstituted $C_5$-$C_{25}$ aryl, a substituted or unsubstituted $C_6$-$C_{25}$ arylalkyl, a straight or branched $C_1$-$C_{30}$ alkoxy group optionally substituted with one or more substituents or two $R^4$ substituents and/or two $R^5$ substituents and/or two $R^6$ substituents on adjacent carbon atoms of the aromatic ring associated therewith can be joined together to form a substituted or unsubstituted $C_3$ to about $C_{30}$ ring, saturated, partially unsaturated or fully unsaturated, optionally substituted with one or more heteroatoms. Lubricating oil compositions containing the tetraaromatic diamine compound additives are also provided.

22 Claims, No Drawings

TETRAAROMATIC DIAMINE COMPOUNDS AS ANTIOXIDANTS

PRIORITY

This application claims the benefit under 35 U.S.C. §119 to U.S. Provisional Application 60/802,975, filed on May 24, 2006, and entitled "TETRAAROMATIC DIAMINE COMPOUNDS AS ANTIOXIDANTS", the contents of which are incorporated by reference herein.

BACKGROUND OF THE INVENTION

1. Technical Field

The present invention generally relates to additives for stabilizing organic products that are subjected to oxidative, thermal, and/or light-induced degradation. More particularly, the present invention relates to a class of tetraaromatic diamine compounds useful as antioxidants.

2. Description of the Related Art

The stabilization of organic materials with antioxidants or other stabilizers are well known to those skilled in the art. For example, in developing lubricating oils, there have been many attempts to provide additives that impart, for example, antioxidant, antiwear, and deposit control properties thereto. Zinc dialkyldithiophosphates (ZDDP) have been used as antifatigue, antiwear, antioxidant, extreme pressure and friction modifying additives for lubricating oils for many years. However, they are subject to several drawbacks owing to their zinc and phosphorus contents. The presence of zinc contributes to the emission of particulates in the exhaust. In addition, during operation of an internal combustion engine, lubricating oil enters the combustion chambers by means such as clinging to cylinder walls as the piston makes its down stroke.

When phosphorus-containing lubricating oil compositions enter the combustion reaction, phosphorus enters the exhaust stream where it acts as a catalyst poison thus shortening the useful life of the catalytic converter. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and environmental reasons, but it is also important to maintain undiminished the antioxidant properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts.

It would therefore be desirable to provide improved additives for stabilizing organic products that are subject to oxidative, thermal, and/or light-induced degradation and in need of stabilization to prevent or inhibit such degradation, e.g., additives for lubricating oils that can improve the antioxidant properties of the oil while reducing the content of zinc and phosphorous of the lubricating oils.

SUMMARY OF THE INVENTION

In accordance with one embodiment of the present invention, a tetraaromatic diamine compound is provided having the general formula:

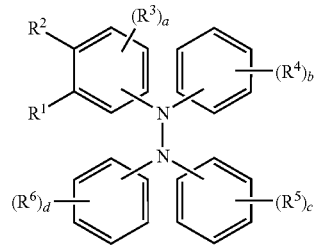

wherein a is 0-3; b, c and d independently are integers from 0-5; $R^1$ and $R^2$ together with the carbon atoms to which they are bonded are joined together to form a substituted or unsubstituted $C_3$ to about $C_{30}$ ring, saturated, partially unsaturated or fully unsaturated, optionally substituted with one or more heteroatoms, $R^3$, $R^4$, $R^5$ and $R^6$ are independently hydrogen, a straight or branched $C_1$-$C_{30}$ alkyl or alkylene group optionally substituted with one or more substituents, a substituted or unsubstituted $C_3$-$C_{12}$ cycloalkyl, a substituted or unsubstituted $C_5$-$C_{25}$ aryl, a substituted or unsubstituted $C_6$-$C_{25}$ arylalkyl, a straight or branched $C_1$-$C_{30}$ alkoxy group optionally substituted with one or more substituents or two $R^4$ substituents and/or two $R^5$ substituents and/or two $R^6$ substituents on adjacent carbon atoms of the aromatic ring associated therewith can be joined together to form a substituted or unsubstituted $C_3$ to about $C_{30}$ ring, saturated, partially unsaturated or fully unsaturated, optionally substituted with one or more heteroatoms.

In accordance with a second embodiment of the present invention, a lubricating oil composition is provided comprising (a) an oil of lubricating viscosity and (b) an antioxidant improving effective amount of at least one tetraaromatic diamine compound having the general formula:

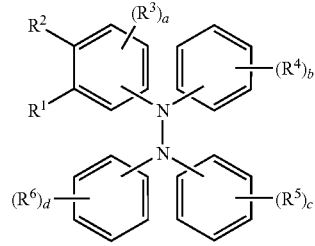

wherein $R^1$, $R^2$, $R^3$, $R^4$, $R^5$, $R^6$, a, b, c and d have the aforestated meanings.

In accordance with a third embodiment of the present invention, a stabilizer-containing composition is provided comprising (a) an organic material subject to oxidative, thermal, and/or light-induced degradation and in need of stabilization to prevent or inhibit such degradation; and (b) a stabilizing effective amount of at least one of at least one tetraaromatic diamine compound having the general formula:

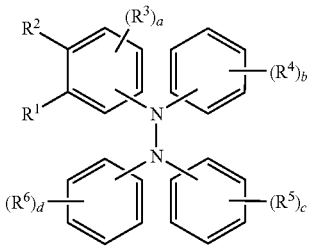

wherein $R^1$, $R^2$, $R^3$, $R^4$, $R^5$, $R^6$, a, b, c and d have the aforestated meanings.

In accordance with a fourth embodiment of the present invention a method for stabilizing an organic material subject to oxidative, thermal, and/or light-induced degradation and in need of stabilization to prevent or inhibit such degradation is provided, the method comprising adding to the organic material a stabilizing effective amount of at least one tetraaromatic diamine compound having the general formula:

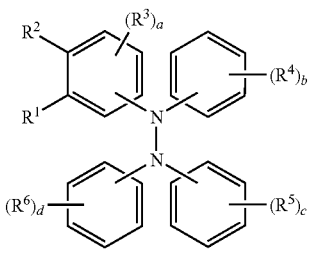

wherein $R^1$, $R^2$, $R^3$, $R^4$, $R^5$, $R^6$, a, b, c and d have the aforestated meanings.

The present invention advantageously provides tetraaromatic diamine compound additives and lubricating oil compositions which provide deposit protection in addition to oxidation-corrosion protection. The lubricating oil compositions can also provide such protection while having relatively low levels of phosphorous, i.e., less than about 0.1%, preferably less than about 0.08% and more preferably less than about 0.05% by weight. Accordingly, the lubricating oil compositions of the present invention can be more environmentally desirable than the higher phosphorous lubricating oil compositions generally used in internal combustion engines because they facilitate longer catalytic converter life and activity while also providing the desired high deposit protection. This is believed to be due to the substantial absence of additives containing phosphorus compounds in these lubricating oil compositions. The tetraaromatic diamine compound additives of this invention may also protect against oxidation both in the presence of transition metals such as, for example, iron (Fe) and Copper (Cu), etc., as well as in a metal free environment.

DETAILED DESCRIPTION OF THE PREFERRED EMBODIMENTS

The tetraaromatic diamine compounds, useful as antioxidants, of the present invention are represented by the general formula 1:

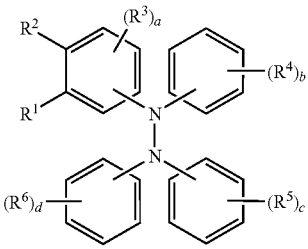

wherein a is 0-3; b, c and d independently are integers from 0-5; $R^1$ and $R^2$ together with the carbon atoms to which they are bonded are joined together to form a substituted or unsubstituted $C_3$ to about $C_{30}$ ring, saturated, partially unsaturated or fully unsaturated, optionally substituted with one or more heteroatoms, including, by way of example, ring structures such as a phenyl ring (to form a naphthalene ring structure with the phenyl ring to which it is attached), cyclopentyl, cyclohexyl (to form a tetralin ring structure with the phenyl ring to which it is attached), optionally substituted with one or more substituents; $R^3$, $R^4$, $R^5$ and $R^6$ are independently hydrogen, a straight or branched $C_1$-$C_{30}$ alkyl or alkylene group optionally substituted with one or more substituents, a substituted or unsubstituted $C_3$-$C_{12}$ cycloalkyl, a substituted or unsubstituted $C_5$-$C_{25}$ aryl, a substituted or unsubstituted $C_6$-$C_{25}$ arylalkyl, a straight or branched $C_1$-$C_{30}$ alkoxy group optionally substituted with one or more substituents, or two $R^4$ substituents and/or two $R^5$ substituents and/or two $R^6$ substituents on adjacent carbon atoms of the aromatic ring associated therewith can be joined together to form a substituted or unsubstituted $C_3$ to about $C_{30}$ ring, saturated, partially unsaturated or fully unsaturated, optionally substituted with one or more heteroatoms including, by way of example, the ring structures discussed above.

Representative examples of heteroatoms for use herein include, by way of example, O, S, N and the like and combinations thereof.

Representative examples of alkyl groups for use herein include, by way of example, a straight or branched hydrocarbon chain radical containing carbon and hydrogen atoms of from 1 to about 30 carbon atoms with or without unsaturation, to the rest of the molecule, e.g., methyl, ethyl, n-propyl, 1-methylethyl (isopropyl), n-butyl, n-pentyl, etc., and the like.

Representative examples of cycloalkyl groups for use herein include, by way of example, a substituted or unsubstituted non-aromatic mono or multicyclic ring system of about 3 to about 12 carbon atoms such as, for example, cyclopropyl, cyclobutyl, cyclopentyl, cyclohexyl, optionally containing one or more heteroatoms.

Representative examples of aryl groups for use herein include, by way of example, a substituted or unsubstituted monoaromatic or polyaromatic radical containing from about 5 to about 25 carbon atoms such as, for example, phenyl, naphthyl, and the like, optionally containing one or more heteroatoms.

Representative examples of arylalkyl groups for use herein include, by way of example, a substituted or unsubstituted aryl group as defined above directly bonded to an alkyl group as defined above which is then attached to the main structure of the monomer at any carbon atom from the alkyl group that results in the creation of a stable structure, e.g., —$CH_2C_6H_5$, —$C_2H_4C_6H_5$ and the like, wherein the aryl group can optionally contain one or more heteroatoms.

Representative examples of alkoxy groups for use herein include, by way of example, a hydrocarbon group such as the alkyl, cycloalkyl, aryl, and arylalkyl as defined above attached via oxygen linkage to the rest of the molecule, i.e., of the general formula —$OR^8$, wherein $R^8$ is an alkyl, cycloalkyl, cycloalkylalkyl, cycloalkenyl, aryl or an arylalkyl group as defined above, e.g., —$OCH_3$, —$OC_2H_5$, or —$OC_6H_5$, and the like.

The substituents in the 'substituted alkyl', 'substituted cycloalkyl', 'substituted aryl', substituted arylalkyl', and 'substituted alkoxy' may be the same or different and include one or more substituents such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, —CO$OR_x$, —$C(O)R_x$, —$C(S)R_x$, —$C(O)NR_xR_y$, —$C(O)ONR_xR_y$, —$NR_xCONR_yR_z$, —$N(R_x)SOR_y$, —$N(R_x)SO_2R_y$, —(=N—N(Rx)R_y), —$NR_xC(O)OR_y$, —$NR_xR_y$, —$NR_xC(O)R_y$—, —$NR_xC(S)R_y$, —$NR_xC(S)NR_yR_z$, —$SONR_xR_y$, —$SO_2NR_xR_y$, —$OR_x$, —$OR_xC(O)NR_yR_z$, —$OR_xC(O)OR_y$—, —$OC(O)R_x$, —$OC(O)NR_xR_y$, —$R_xNR_yC(O)R_z$, —$R_xOR_y$, —$R_xC(O)OR_y$, —$R_xC(O)NR_yR_z$, —$R_xC(O)R_x$, —$R_xOC(O)R_y$, —$SR_x$, —$SOR_x$, —$SO_2R_x$, —$ONO_2$, wherein $R_x$, $R_y$ and $R_z$ in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

In one embodiment, the tetraaromatic diamine compounds of this invention can be where $R^1$ and $R^2$ are joined together to form a substituted or unsubstituted, saturated or partially or fully unsaturated 5-, 6-, or 7-membered ring optionally substituted with one or more heteroatoms. In another embodiment, the tetraaromatic diamine compounds of this invention can be where two $R^4$ substituents and/or two $R^5$ substituents and/or two $R^6$ substituents on adjacent carbon atoms of the aromatic ring associated therewith are joined together to form a substituted or unsubstituted, saturated or partially or fully unsaturated $C_3$ to about $C_{30}$ ring optionally substituted with one or more heteroatoms. In yet another embodiment, the tetraaromatic diamine compounds of this invention can be where two $R^4$ substituents and/or two $R^5$ substituents and/or two $R^6$ substituents on adjacent carbon atoms of the aromatic ring associated therewith are joined together to form a substituted or unsubstituted, unsaturated, saturated or partially or fully unsaturated 5-, 6-, or 7-membered ring optionally substituted with one or more heteroatoms. In still yet another embodiment, the tetraaromatic diamine compounds of this invention can be where $R^1$ and $R^2$ are joined together to form a substituted or unsubstituted and saturated or partially or fully unsaturated 5-, 6-, or 7-membered ring optionally substituted with one or more heteroatoms and two $R^4$ substituents and/or two $R^5$ substituents and/or two $R^6$ substituents on adjacent carbon atoms of the aromatic ring associated therewith are joined together to form a substituted or unsubstituted and saturated or partially or fully unsaturated 5-, 6-, or 7-membered ring optionally substituted with one or more heteroatoms.

The tetraaromatic diamine compounds of this invention can be obtained by the oxidation of the corresponding substituted diphenyl amines with an oxidizing agent under suitable reaction conditions to form the compounds herein. Useful oxidizing agents include, but are not limited to, $Na_2Cr_2O_7$/AcOH or $KMnO_4$, $PbO_2$, AgO, tert-butyl peroxide and the like. The temperature for this reaction will ordinarily range from about 10° C. to about 80° C. and more preferably from about 20° C. to about 40° C. If desired, the reaction can be carried out in a suitable solvent. Suitable solvents include, but are not limited to, aliphatic hydrocarbons, e.g., hexane and the like; aromatic hydrocarbons, e.g., toluene, xylene, benzene and the like; ketones, e.g., acetone and the like; halogenated hydrocarbons, e.g., dichloromethane, chloroform, and the like and mixtures thereof.

The tetraaromatic diamine compounds of this invention may have useful antioxidant properties for use as antioxidants in, for example, compounded tires, polyols, plastics, urethanes, greases, motor oils, rubber belts, cables, gaskets, seals, rubber products in the garment and carpet industries. Accordingly, an embodiment of the present invention is a stabilizer-containing composition containing an organic material subject to oxidative, thermal, and/or light-induced degradation and in need of stabilization to prevent or inhibit such degradation and, as a stabilizer therefore, the foregoing tetraaromatic diamine compounds. The tetraaromatic diamine compound stabilizers can be added to the organic material in an amount sufficient to impart an appreciable stabilizing effect. In general, this amount may vary from about 0.1 wt. % to about 5 wt. % weight percent, preferably from about 0.5 wt. % to about 3 wt. % weight percent and more preferably from about 0.5 wt. % to about 2.0 wt. % by total weight of the organic material.

Another embodiment of the present invention is a lubricating oil composition containing at least (a) an oil of lubricating viscosity and (b) an effective amount of at least one of the foregoing tetraaromatic diamine compounds. Generally, the oil of lubricating viscosity for use in the lubricating oil compositions may be present in a major amount, e.g., an amount of greater than about 50 wt. %, preferably greater than about 70 wt. %, more preferably from about 80 to about 99.5 wt. % and most preferably from about 85 to about 98 wt. %, based on the total weight of the composition. The oil of lubricating viscosity for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, e.g., automatic transmission fluids, etc. turbine lubricants, compressor lubricants, metal-working lubricants, and other lubricating oil and grease compositions. Additionally, the oil of lubricating viscosity for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the oil of lubricating viscosity is dependent upon the application. Accordingly, the viscosity of an oil of lubricating viscosity for use herein will ordinarily range from about 2 to about 2000 centistokes (cSt) at 100° Centigrade (C). Generally, individually the oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable oil of lubricating viscosity is one that comprises little, if any, heavy fraction; e.g., little, if any, lube oil fraction of viscosity about 20 cSt or higher at 100° C.

The oil of lubricating viscosity may be derived from natural lubricating oils, synthetic lubricating oils or mixtures thereof. Suitable oils includes base stocks obtained by isomerization of synthetic wax and slack wax, as well as hydrocracked base stocks produced by hydrocracking (rather than solvent extracting) the aromatic and polar components of the crude. Suitable oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and their derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils includes, but is not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of about 1,000, diphenyl ether of polyethylene glycol having a molecular weight of about 500 to about 1000, diethyl ether of polypropylene glycol having a molecular weight of about 1,000 to about 1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The oil of lubricating viscosity may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Refined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The tetraaromatic diamine compound additives of this invention can be used as a complete or partial replacement for commercially available antioxidants currently used in lubricant formulations and can be in combination with other additives typically found in motor oils and fuels. When used in combination with other types of antioxidants or additives used in oil formulations, synergistic and/or additive performance effects may also be obtained with respect to improved antioxidancy, antiwear, frictional and detergency and high temperature engine deposit properties. Such other additives can be any presently known or later-discovered additives used in formulating lubricating oil compositions. The lubricating oil additives typically found in lubricating oils are, for example, dispersants, detergents, corrosion/rust inhibitors, antioxidants, anti-wear agents, anti-foamants, friction modifiers, seal swell agents, emulsifiers, VI improvers, pour point depressants, and the like. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of other antioxidants include alkylated diphenylamines, N-alkylated phenylenediamines, phenyl-naphthylamine, alkylated phenyl-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. Representative examples of such additives are those commercially available from such sources as Chemtura Corporation and include, for example, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, Naugalube 420 and the like.

Examples of anti-wear additives that can be used in combination with the additives of the present invention include organo borates, organo phosphites, organo phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. Representative examples of such additives are those commercially available from The Lubrizol Corporation such as Lubrizol 677A, Lubrizol 1095, Lubrizol 1097, Lubrizol 1360, Lubrizol 1395, Lubrizol 5139, Lubrizol 5604 and the like, and from Ciba Corporation such as Irgalube 353 and the like.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. Representative examples of such friction modifiers are those commercially available from R.T. Vanderbilt Company, Inc. such as Molyvan A, Molyvan L, Molyvan 807, Molyvan 856B, Molyvan 822, Molyvan 855, and the like; Asahi Denka Kogyo K.K. such as SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, and the like; and from Akzo Nobel Chemicals GmbH such as Ketjen-Ox 77M, Ketjen-Ox 77TS, and the like.

An example of an anti-foam agent is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dihydrocarbyl dithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

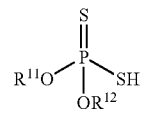

wherein $R^{11}$ and $R^{12}$ are the same or different and can be linear or branched alkyl, cycloalkyl, aralkyl, alkaryl, or substituted substantially hydrocarbyl radical derivatives of any of the above groups, and wherein the $R^{11}$ and $R^{12}$ groups in the acid each have, on average, at least 3 carbon atoms. By "substantially hydrocarbyl" is meant radicals containing substituent groups, e.g., 1 to 4 substituent groups per radical moiety such as, for example, ether, ester, thio, nitro, or halogen, that do not materially affect the hydrocarbon character of the radical.

Specific examples of suitable $R^{11}$ and $R^{12}$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, beta-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R^{11}$ and $R^{12}$ radicals are alkyl of from 4 to about 18 carbon atoms.

The phosphorodithioic acids are readily obtainable by the reaction of a phosphorus pentasulfide and an aliphatic alcohol and/or phenol. The reaction involves at least mixing, at a temperature ranging from about 20° C. to 200° C., about 4 moles of the alcohol or phenol with one mole of phosphorus pentasulfide. Hydrogen sulfide can be liberated as the reaction takes place. Mixtures of alcohols, phenols, or both can be employed, e.g., mixtures of $C_3$ to $C_{30}$ alcohols, $C_6$ to $C_{30}$ aromatic alcohols, etc. The metals useful to make the phosphate salts include, but are not limited to, Group I metals, Group II metals, aluminum, lead, tin, molybdenum, manganese, cobalt, and nickel with zinc being the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate and the like and mixtures thereof.

In some instances, the incorporation of certain ingredients, particularly carboxylic acids or metal carboxylates, e.g., small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art. See, e.g., U.S. Pat. Nos. 3,293,181; 3,397,145; 3,396,109; and 3,442,804; the disclosures of which are hereby incorporated by reference. Also useful as anti-wear additives are amine derivatives of dithiophosphoric acid compounds, such as are described in U.S. Pat. No. 3,637,499, the disclosure of which is hereby incorporated by reference in its entirety.

The zinc salts are most commonly used as anti-wear additives in lubricating oils in amounts ranging from about 0.1 to about 10, preferably about 0.2 to about 2 wt. %, based upon the total weight of the lubricating oil composition. They may be prepared in accordance with known techniques, e.g., by first forming a dithiophosphoric acid, usually by reaction of an alcohol and/or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

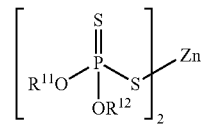

wherein $R^{11}$ and $R^{12}$ have the aforestated meanings.

The lubricating oil compositions of the present invention, when they contain these additives, are typically blended into a base oil in amounts such that the additives therein are effective to provide their normal attendant functions. Representative effective amounts of such additives are illustrated in Table 1.

TABLE 1

| Additives | Preferred Weight % | More Preferred Weight % |
|---|---|---|
| V.I. Improver | about 1 to about 12 | about 1 to about 4 |
| Corrosion Inhibitor | about 0.01 to about 3 | about 0.01 to about 1.5 |
| Oxidation Inhibitor | about 0.01 to about 5 | about 0.01 to about 1.5 |
| Dispersant | about 0.1 to about 10 | about 0.1 to about 5 |
| Lube Oil Flow Improver | about 0.01 to about 2 | about 0.01 to about 1.5 |
| Detergent/Rust Inhibitor | about 0.01 to about 6 | about 0.01 to about 3 |
| Pour Point Depressant | about 0.01 to about 1.5 | about 0.01 to about 0.5 |
| Anti-foaming Agents | about 0.001 to about 0.1 | about 0.001 to about 0.01 |
| Anti-wear Agents | about 0.001 to about 5 | about 0.001 to about 1.5 |
| Seal Swell Agents | about 0.1 to about 8 | about 0.1 to about 4 |
| Friction Modifiers | about 0.01 to about 3 | about 0.01 to about 1.5 |
| Lubricating Base Oil | Balance | Balance |

When other additives are employed, it may be desirable, although not necessary, to prepare additive concentrates comprising concentrated solutions or dispersions of the tetraaromatic diamine compound additives of this invention (in concentrate amounts hereinabove described), together with one or more other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by, for example, solvents and by mixing accompanied by mild heating, but this is not essential.

The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the Al weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive in a carrier or diluent oil of lubricating oil viscosity.

The following non-limiting examples are illustrative of the present invention.

EXAMPLE 1

This example illustrates the preparation of a compound of the formula.

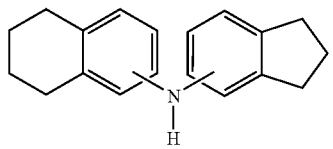

Bromination

To a well stirred mixture of tetralin (360 g, 2.7 mol) and iodine (1 g) cooled in an ice bath was slowly added bromine (470 g, 2.9 mol) over a 3 hour period maintaining an internal temperature of 0-10° C. (note: vigorous evolution of HBr quenched by sodium hydroxide scrubber). The mixture was left to warm to room temperature and stirred overnight. The mixture was then poured into a cooled (5° C.) saturated solution (1.5 liters) of sodium sulfite, stirred for 40 minutes and extracted with $CH_2Cl_2$ twice (500 mL, 200 mL). The combined extracts were dried over sodium sulfate and concentrated on a rotovap. The residue was distilled under vacuum. A forerun of mostly starting material was collected up to 760° C. at 1.3-0.58 T. The product was distilled at 73-86° C. at 0.3-0.6 T as a mixture of isomers (collected in several fractions for a total of ~450 g).

Coupling

A mixture of the 2-aminoindan (39.8 g, 0.30 mol), tetralin bromide (65 g, 0.30 mol) and 50% NaOH (22 mL) in toluene (220 mL) was purged with nitrogen for 45 minutes. Bis(tri-t-butylphosphine)palladium(0) (0.8 g, 0.0016 mol) and cetyl-trimethylammonium bromide (0.28 g, 0.0008 mol) were added to the flask under a stream of nitrogen. The mixture was then heated at about 100° C. for 16 hours. TLC analysis indicated little reaction so another portion of catalyst (0.8 g) and phase-transfer agent (0.28 g) was added and the reaction was continued. After an additional 4 hours, TLC indicated about 80% conversion. The mixture was heated for an additional 3 days and then left to cool overnight without stirring. The mixture was filtered through Celite and the filter cake rinsed with toluene. The solution was extracted with water (100 mL) and concentrated on a rotovap. The resulting residue was distilled on a short-path Kugelrohr apparatus with a vacuum. A forerun fraction was collected up to 140° C. at 0.89 T. After further heating to 160° C. (at 0.6-3.6 T), the product (73 g) was distilled as a yellow oil which solidified on standing. GC/FID analysis indicated a purity of 98.7% (by area %) and a 3:1 ratio of the two isomeric products. This reaction is generally shown below in Scheme I.

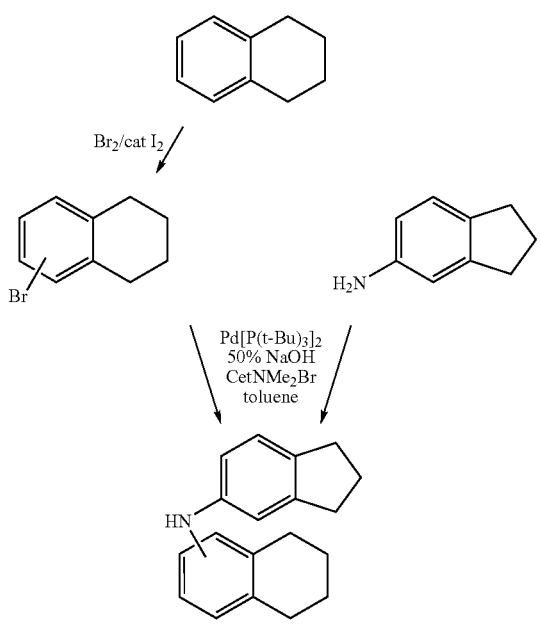

EXAMPLE 2

This example illustrates the preparation of a compound of the formula

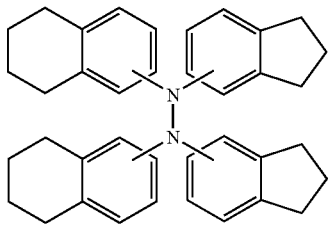

Into a 250 mL round bottom flask was added 5.33 grams of the tetralin-indan amine of Example 1 (3:1 ratio of two regio-isomers, $C_{19}H_{21}N$, $M_n=263.38$, 20.24 mmol, 1.00 eq.) under ambient condition. Next, 15 gram AgO ($M_n=123.87$, 242.19 mmol, 11.97 eq.) and 50 mL acetone were added to the flask. After 24 hours, the mixture was filtered to remove all solid and the residue solid was washed with 10 mL acetone. The solvent was removed via vacuum distillation to provide a product as a light brownish solid.

Formula: $C_{38}H_{40}N_2$, $M_n=524.75$

Yield: 5.1 gram, 96%

EXAMPLE 3

Preparation of Lubricating Oil Composition

To a motor oil formulation was blended 0.4 weight percent of the compound of Example 2 and an additional 0.1 wt. % of Solvent Neutral 150 base oil along with 50 ppm ferric naphthenate to form a lubricating oil composition. The motor oil formulation is set forth in Table 2.

TABLE 2

Motor Oil Formulation (Base Blend)

| | wt % |
|---|---|
| Solvent Neutral 150 | 83.85 |
| Zinc Dialkyldithiophosphate | 1.01 |
| Succinimide Dispersant | 7.58 |
| Overbased Calcium Sulfonate Detergent | 1.31 |
| Neutral Calcium Sulfonate Detergent | 0.5 |
| Antioxidant | 0.0 |
| Rust Inhibitor | 0.1 |
| Pour Point Depressant | 0.1 |
| OCP VI Improver | 5.55 |

COMPARATIVE EXAMPLE A

Preparation of a Lubricating Oil Composition

To the motor oil formulation set forth in Table 2 was added an additional 0.5 wt. % of Solvent Neutral 150 base oil along with 50 ppm ferric naphthenate to form a lubricating oil composition.

Testing

The antioxidant properties of the lubricating oil composition of Example 3 was evaluated and compared to the antioxidant properties of Naugalube 438 L (Nonylated diphenylamine, commercially available from Chemtura Corporation, Middlebury, Conn.) and the lubricating oil composition of Comparative Example A using the Pressurized Differential Scanning Calorimetry (PDSC) test and the Thermo-Oxidation Engine Oil Simulation Test (TEOST) as described below.

Pressurized Differential Scanning Calorimetry (PDSC)

The PDSC measures the relative oxidation induction time (OIT) of antioxidants in a lubricating oil composition as measured in $O_2$ gas under pressure. The PDSC instrument used is a Mettler DSC27HP manufactured by Mettler-Toledo, Inc (Switzerland). The PDSC method employs a steel cell under constant oxygen pressure throughout each run. The instrument has a typical repeatability of ±2.5 minutes with 95 percent confidence over an OIT of 100 minutes. The PDSC test conditions are given in Table 35. At the beginning of a PDSC run, the steel cell is pressurized with oxygen and heated at a rate of 40° C. per minute to the prescribed isothermal temperature. The induction time is measured from the time the sample reaches its isothermal temperature until the enthalpy change is observed. The longer the oxidation induction time, the better the oxidation stability of the oil. The OIT results of the lubricating oil compositions of Example 3 and Comparative Example A and Naugalube 438L are set forth in Table 4.

TABLE 3

PDSC Test Conditions

| Test Parameters | Settings |
|---|---|
| Temperature | 200° C. |
| Gas | Oxygen |
| Flow Rate | 100 mL/minute |

TABLE 3-continued

PDSC Test Conditions

| Test Parameters | Settings |
|---|---|
| Pressure | 500 psi |
| Sample Size | 1-5 mg |
| Pan (open/closed) | open |

TABLE 4

PDSC Results

| Ex./Comp. Ex. | Time, minutes |
|---|---|
| Example 3 | 18.7 |
| Naugalube 438L | 16.7 |
| Comp. Ex. A | 4.5 |

It can be seen from the above data that a lubricating oil composition containing the compound within the scope of the present invention exhibited significantly better oxidative stability than a lubricating oil composition containing no antioxidant.

Mid-High Temperature Thermo-Oxidative Engine Oil Simulation Test

The Mid-High Temperature Thermo-oxidative Engine Oil Simulation Test (MHT TEOST) was performed to determine the deposit forming tendencies of the motor engine oil. The improved thermal deposit control of the additives of this invention in stabilizing the engine oil formulation has been clearly demonstrated by the MHT TEOST. This test determines the mass of deposit formed on a specially constructed steel rod by continuously stressing a repetitive passage of 8.5 ml of test oil under thermal-oxidative and catalytic conditions. The instrument used was manufactured by Tannas Co. and has a typical repeatability of 0.15 (x+16) mg wherein x is the mean of two or more repeated test results. The TEOST test conditions are listed in Table 5. The less the amount of deposits obtained, the better the oxidation stability of the oil. The results of this test are set forth in Table 6.

TABLE 5

TEOST MHT Test Conditions

| Test Parameters | Settings |
|---|---|
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

TABLE 6

TEOST Results

| Ex./Comp. Ex. | mg deposits |
|---|---|
| Example 3 | 35.5 |
| Naugalube 438L | 71.2 |
| Comp. Ex. A | 108 |

It can be seen from the above data that the addition of a compound within the scope of the present invention to a lubricating oil composition significantly reduces the total deposit mass of the base blend formulation.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A tetraaromatic diamine compound having the general formula:

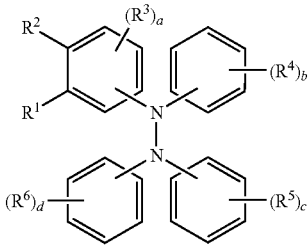

wherein a is 0-3;
b, c and d independently are integers from 0-5,
$R^1$ and $R^2$ together with the carbon atoms to which they are bonded are joined together to form a saturated or partially saturated $C_3$ to about $C_{30}$ ring,
$R^3$, $R^4$, $R^5$ and $R^6$ are independently hydrogen, a straight or branched $C_1$-$C_{30}$ alkyl or alkylene group optionally substituted with one or more substituents, a substituted or unsubstituted $C_3$-$C_{12}$ cycloalkyl, a substituted or unsubstituted $C_5$-$C_{25}$ aryl, a substituted or unsubstituted $C_6$-$C_{25}$ arylalkyl, a straight or branched $C_1$-$C_{30}$ alkoxy group optionally substituted with one or more substituents.

2. The tetraaromatic diamine compound of claim 1, wherein $R^1$ and $R^2$ are joined together to form a saturated 5-, 6-, or 7-membered ring.

3. The tetraaromatic diamine compound of claim 1, wherein $R^1$ and $R^2$ are joined together to form a partially unsaturated 5-, 6-, or 7-membered ring.

4. The tetraaromatic diamine compound of claim 1, wherein two $R^4$ substituents and two $R^5$ substituents and two $R^6$ substituents on adjacent carbon atoms of the aromatic ring associated therewith are joined together to form a saturated or partially unsaturated $C_3$ to about $C_{30}$ ring.

5. The tetraaromatic diamine compound of claim 1, wherein two substituents and two $R^5$ substituents and two $R^6$ substituents on adjacent carbon atoms of the aromatic ring associated therewith are joined together to form a saturated 5-, 6-, or 7-membered ring.

6. The tetraaromatic diamine compound of claim 1, wherein two $R^4$ substituents and two $R^5$ substituents and two $R^6$ substituents on adjacent carbon atoms of the aromatic ring associated therewith are joined together to form a partially unsaturated 5-, 6-, or 7-membered ring.

7. The tetraaromatic diamine compound of claim 1, wherein $R^1$ and $R^2$ are joined together to form a saturated or partially unsaturated 5-, 6-, or 7-membered ring and two $R^4$ substituents and two $R^5$ substituents and two $R^6$ substituents on adjacent carbon atoms of the aromatic ring associated therewith are joined together to form a substituted or unsubstituted and saturated or partially unsaturated 5-, 6-, or 7-membered ring.

8. A lubricating oil composition comprising
(a) at least one oil of lubricating viscosity and
(b) an antioxidant improving effective amount of at least one tetraaromatic diamine compound having the general formula:

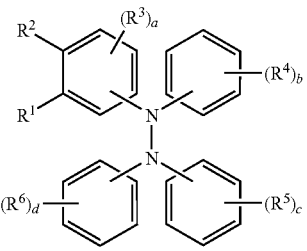

wherein a is 0-3;
b, c and d independently are integers from 0-5,
$R^1$ and $R^2$ together with the carbon atoms to which they are bonded are joined together to form a saturated or partially saturated $C_3$ to about $C_{30}$ ring
$R^3$, $R^4$, $R^5$ and $R^6$ are independently hydrogen, a straight or branched $C_1$-$C_{30}$ alkyl or alkylene group optionally substituted with one or more substituents, a substituted or unsubstituted $C_3$-$C_{12}$ cycloalkyl, a substituted or unsubstituted $C_5$-$C_{25}$ aryl, a substituted or unsubstituted $C_6$-$C_{25}$ arylalkyl, a straight or branched $C_1$-$C_{30}$ alkoxy group optionally substituted with one or more substituents.

9. The lubricating oil composition of claim 8, wherein in the tetraaromatic diamine compound $R^1$ and $R^2$ are joined together to form a saturated 5-, 6-, or 7-membered ring.

10. The lubricating oil composition of claim 8, wherein in the tetraaromatic diamine compound $R^1$ and $R^2$ are joined together to form a partially unsaturated 5-, 6-, or 7-membered ring.

11. The lubricating oil composition of claim 1, wherein two $R^4$ substituents and two $R^5$ substituents and two $R^6$ substituents on adjacent carbon atoms of the aromatic ring associated therewith are joined together to form a saturated or partially unsaturated $C_3$ to about $C_{30}$ ring.

12. The lubricating oil composition of claim 8, wherein in the tetraaromatic diamine compound $R^1$ and $R^2$ are joined together to form a saturated or partially unsaturated 5-, 6-, or 7-membered ring and two $R^4$ substituents and two $R^5$ substituents and two $R^6$ substituents on adjacent carbon atoms of the aromatic ring associated therewith are joined together to form a saturated or partially unsaturated 5-, 6-, or 7-membered ring.

13. The lubricating oil composition of claim 8, wherein the at least one oil of lubricating viscosity is selected from the group consisting of engine oils, transmission fluids, hydraulic fluids, gear oils, marine cylinder oils, compressor oils, refrigeration lubricants and mixtures thereof.

14. The lubricating oil composition of claim 8, further comprising at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

15. The lubricating oil composition of claim 8, further comprising at least one lubricating oil additive selected from the group consisting of an alkylated diphenylamine, alkylated hindered phenolic, alkylated substituted or unsubstituted phenylenediamine, alkylated oil soluble copper compound, alkylated sulfur containing compound known to impart oxidation stability and mixtures thereof.

16. The lubricating oil composition of claim 15, wherein the alkylated sulfur containing compound known to impart oxidation stability is selected from the group consisting of phenothiazines, sulfurized olefins, thiocarbamates, sulfur bearing hindered phenolics, zinc dialkyldithiophosphates and mixtures thereof.

17. The lubricating oil composition of claim 8, having a phosphorous content of less than about 0.1 weight percent.

18. An additive package comprising about 1 to about 75 weight of at least one tetraaromatic diamine compound of claim 1.

19. A stabilizer-containing composition comprising (a) an organic material subject to oxidative, thermal, and/or light-induced degradation and in need of stabilization to prevent or inhibit such degradation; and (b) a stabilization effective amount of at least one tetraaromatic diamine compound of claim 1.

20. A method for stabilizing an organic material subject to oxidative, thermal, and/or light-induced degradation and in need of stabilization to prevent or inhibit such degradation, the method comprising adding to the organic material a stabilizing amount of at least one tetraaromatic diamine compound of claim 1.

21. The tetraaromatic diamine compound of claim 1, wherein two $R^4$ substituents and/or two $R^5$ substituents and/or two $R^6$ substituents on adjacent carbon atoms of the aromatic ring associated therewith are joined together to form a saturated or partially saturated $C_3$ to about $C_{30}$ ring.

22. The lubricating oil composition of claim 8, wherein two $R^4$ substituents and/or two $R^5$ substituents and/or two $R^6$ substituents on adjacent carbon atoms of the aromatic ring associated therewith are joined together to form a saturated or partially saturated $C_3$ to about $C_{30}$ ring.

\* \* \* \* \*